(12) United States Patent
Yamaguchi et al.

(10) Patent No.: US 6,169,114 B1
(45) Date of Patent: Jan. 2, 2001

(54) ENDERMIC LINIMENT CONTAINING A THIOL COMPOUND AND ZINC OXIDE

(75) Inventors: Kenji Yamaguchi; Eiichiro Yagi, both of Yokohama; Masako Naganuma, Tokyo; Masato Hatao; Ichiro Iwai, both of Yokohama, all of (JP)

(73) Assignee: Shiseido Company, Ltd., Tokyo (JP)

( * ) Notice: Under 35 U.S.C. 154(b), the term of this patent shall be extended for 0 days.

(21) Appl. No.: 09/284,959

(22) PCT Filed: Sep. 22, 1998

(86) PCT No.: PCT/JP98/04274

§ 371 Date: May 5, 1999

§ 102(e) Date: May 5, 1999

(87) PCT Pub. No.: WO99/16411

PCT Pub. Date: Apr. 8, 1999

(30) Foreign Application Priority Data

Sep. 26, 1997 (JP) .................................... 9-279507

(51) Int. Cl.[7] .......................... A61K 31/195; A61K 7/00; A61K 9/14; A61K 9/50

(52) U.S. Cl. .......................... 514/562; 424/401; 424/489; 424/499; 424/67

(58) Field of Search ...................... 424/401, 552, 424/59, 69; 514/529, 552, 679, 562

(56) References Cited

U.S. PATENT DOCUMENTS

| 5,545,399 | * | 8/1996 | Lee et al. ............................... 424/59 |
| 5,691,380 | * | 11/1997 | Mason et al. ........................ 514/562 |
| 5,733,535 | * | 3/1998 | Hollingshead et al. ................ 424/65 |

FOREIGN PATENT DOCUMENTS

9102538  *  7/1991  (WO) ........................... A61K 37/12

* cited by examiner

Primary Examiner—William R. A. Jarvis
Assistant Examiner—Vickie Kim
(74) Attorney, Agent, or Firm—Townsend & Banta

(57) ABSTRACT

The present invention is an endermic liniment which characteristically contains a thiol compound and zinc oxide. An endermic liniment which can contain a thiol compound in a stable manner can be provided by blending in a thiol compound and zinc oxide.

5 Claims, No Drawings

ENDERMIC LINIMENT CONTAINING A THIOL COMPOUND AND ZINC OXIDE

FIELD OF THE INVENTION

This invention relates in general to an endermic liniment, and more particularly to an endermic liniment which can contain a thiol compound in a stable manner.

BACKGROUND OF THE INVENTION

A thiol compound is generally very unstable when exposed to light, heat, and oxygen, and therefore an endermic liniment which contains a thiol compound has the shortcoming of being easily oxidized by light, heat, or oxygen and thus losing its medicinal efficacy. Such compounds therefore must be stored in a cool, light free place or an airtight, sealed container, and its appication forms are significantly limited.

Also, the original thiol compound generally has a unpleasant odor and, when it is dissolved in an aqueous solution, produces a significantly offensive odor derived from sulfur, which limits the amount that can be blended into the endermic liniment.

Therefore, when blending a thiol compound in an endermic liniment, it was necessary to prevent the decomposition of the thiol compound by using an expensive light blocking container, a container with low oxygen permeability, or a container with high sealing performance, or by preparing it at the time of use.

If, despite such countermeasures, decomposition cannot be prevented and the unpleasant odor occurs, then there are limitations such as having to lower the blend ratio.

Based on the above mentioned problems, the inventors conducted earnest research and discovered that the occurrence of unpleasant odor due to light, heat, oxidation, etc. can be prevented and thiol compounds can be blended in a stable manner by blending the thiol compounds together with zinc oxide in an endermic liniment, thus completing the present invention.

The object of the present invention is to provide an endermic liniment which can contain a thiol compound in a stable manner.

DISCLOSURE OF THE INVENTION

That is, the present invention provides an endermic liniment which characteristically contains a thiol compound and zinc oxide.

Also, the present invention provides the aforementioned endermic liniment wherein said thiol compound is one or more types of glutathione and its derivatives.

Furthermore, the present invention provides the aforementioned endermic liniment wherein said thiol compound is one or more types of cysteine and its derivatives.

Also, the present invention provides the aforementioned endermic liniment wherein the average particle size of said zinc oxide is 0.2 micrometers or less.

Furthermore, the present invention provides the aforementioned endermic liniment wherein the content of said thiol compound is 0.001–20.0 wt % of the total endermic liniment.

Also, the present invention provides the aforementioned endermic liniment wherein the content of said zinc oxide is 0.01–50.0 wt % of the total endermic liniment.

THE BEST MODES OF THE EMBODIMENTS

The configuration of the present invention is described below.

Examples of the thiol compound used in the present invention include glutathione, acetylized glutathione, glutathione hydrochloride, phosphate, and sulfate, cysteine, N-acetyl cysteine, cysteine hydrochloride, cysteine sulfate, and cysteine phosphate, which are cysteine containing amino acid derivatives, as well as mercapto acetic acid, mercapto propionic acid, ammonium thiolactate and monoethanolamine thiolactate.

The thiol compound to be blended into the endermic liniment is selected based on the application of the endermic liniment. In general, a thiol compound has a reducing action and therefore is used as an antioxidant. In terms of usability, safety, and the efficacy, the preferable are glutathione and its derivatives as well as cysteine and its derivatives, which are amino acid-type compounds. The most preferable are glutathione and N-acetyl cysteine.

The blend ratio of the thiol compound varies depending on the application of the endermic liniment, but the blend ratio range is usually 0.001–20.0 wt % of the total endermic liniment. The endermic liniment of the present invention exhibits the significant effect of the present invention when the blend ratio is 0.1 wt % or more, preferably 1 wt % or more.

Zinc oxide used in the present invention acts as a stabilizer of the thiol compound. Specific examples include zinc flower, fine particle zinc oxide and ultra fine particle zinc oxide.

For the zince oxide, powder, fine powder in particular, is preferable. The finer the powder, the higher the effect of stabilizing the thiol compound. Considering the usability, the average particle size of the zinc oxide is preferably 0.001–0.2 micrometers, and more preferably 0.00 5–0.1 micrometers. Examples of the commercial products include ultra-fine particle zinc oxide FINEX75, FINEX50, and FINEX25 (Sakai Chemical Industry Co., Ltd.).

Zinc oxide with a water repellent treatment on its surface can also be used in the present invention. Examples of the water repellent treatment include the myristic acid treatment, zinc myristate treatment, aluminum myristate treatment, palmitic acid treatment, dextrin palmitic acid treatment, zinc palmitate treatment, aluminum palmitate treatment, stearic acid treatment, dextrin stearic acid treatment, zinc stearate treatment, aluminum stearate treatment, and silicone treatment, etc.

The blend ratio of zinc oxide is preferably 0.01–50.0 wt %, more preferably 0.05–20 wt %, of the total endermic liniment. If it is less than 0.01 wt % then the effect of the present invention may not be exhibited sufficiently. If it is more than 50 wt % then there may be adverse effects on the stability of base agent.

In the present invention, the stability of the thiol compound improves if an antioxidant is blended in addition to the aforementioned essential ingredients. The antioxidants that can be blended include BHT (dibutylhydroxytoluene), BHA (butylhydroxyanisol), gallic esters and their derivatives, and NDGA (nordihydroguaiaretic acid), among which BHT and BHA are particularly preferable.

The blend ratio of the antioxidant in the endermic liniment depends on the blend ratios of the thiol compound and zinc oxide. Usually, 0.001–10.0 wt % of the total endermic liniment is preferable. A more preferable range is 0.01–2 wt %.

In the present invention, blending zinc oxide in an endermic liniment containing a thiol compound prevents the unpleasant smell from the thiol compound and allows the thiol compound to be stable. Therefore, the endermic liniment of the present invention prevents the unpleasant smell due to light, heat, oxygen, etc., and has improved stability. Because of this, there are the following advantages: light blocking containers, containers with low oxygen permeability, containers with high sealing performance, etc., which are conventionally necessary, are not required, and the blend ratio of the thiol compound can be selected based on the purpose.

The endermic liniment of the present invention can contain medicinally effective ingredients other than the aforementioned thiol compound such as humectants, whitening agents, antiinflammatories, activating agents, blood flow promoting agents, antiseborrheac agents, plant extracts, various vitamins, etc., as well as other ingredients which can normally be contained in an endermic liniment, within the range that doesn't affect the effect of the present invention.

"Endermic liniment" in the present invention refers to cosmetics, drugs, quasi-drugs, etc. which are applied on the epidermis. It can comprise a wide variety of formulations including an aqueous solution system, solubilized system, emulsified system, powder system, oil-liquid system, gel system, ointment system, aerozol system, water-oil two-phase system, and water-oil-powder three-phase system. In the basic cosmetic area, it can be utilized in the aforementioned various formulations in product forms such as cleansing agents, toilet water, emulsions, creams, gels, essences (cosmetic lotion), pack masks, etc. In the makeup cosmetic area, it can be widely utilized in product forms such as foundations. In the drug or quasi-drug area, it can be widely utilized in product forms such as various ointments. The endermic liniment of the present invention is not limited in terms of the formulation and the product form.

The endermic liniment of the present invention can be prepared with a conventional method by blending, in addition to the aforementioned essential ingredients, prior art base agent ingredients normally used in a endermic liniment within the range which does not affect the effect of the present invention and according to the aforementioned desired formulations and product forms.

Examples of the ingredients to be blended include liquid fats/oils including avocado oil, tsubaki oil, evening primrose oil, turtle oil, macadema nut oil, corn oil, mink oil, olive oil, rape seed oil, egg yolk oil, sesame seed oil, persic oil, wheat germ oil, sasanqua oil, castor oil, linseed oil, safflower oil, cotton seed oil, perilla oil, soy bean oil, peanut oil, tea seed oil, kaya oil, rice bran oil, chinese tung oil, Japanese tung oil, jojoba oil, germ oil, triglycerol glyceryl trioctanoate and glyceryl triisopalmitate; solid fats/oils including cacao butter, coconut oil, horse tallow, hardened coconut oil, palm oil, beef tallow, sheep tallow, hardened beef tallow, palm kernel oil, pork tallow, beef bone tallow, Japanese core wax, hardened oil, neatsfoot tallow, Japanese wax and hardened castor oil; waxes including honeybee wax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether; hydrocarbon oils including liquid paraffin, ozokerite, squalene, pristane, paraffin, ceresin, squalene, vase line and microcrystalline wax; higher fatty acids including lauric acid, myristic acid, palmitic acid, stearic acid, behenic acid, oleic acid, 12-hydroxystearic acid, undecylenic acid, tall oil, isostearic acid, linoleic acid, linolenic acid, eicosapentaenoic acid (EPA) and docosahexaenoic acid (DHA); higher alcohols such as linear chain alcohols including lauryl alcohol, cetyl alcohol, stearyl alcohol, behenyl alcohol, myristyl alcohol, oleyl alcohol and cetostearyl alcohol, and branched chain alcohols including monostearylglycerol ether (batyl alcohol), 2-decyltetradecynol, lanolin alcohol, cholesterol, phytosterol, hexyldodecanol, isostearyl alcohol and octyldodecanol; synthetic ester oils including isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprylate, diisostearyl malate, glyceryl di-2-heptylundecanoate, trimethylolpropane tri-2-ethylhexylate, trimethylolpropane triisostearate, pentaneerythritol tetra-2-ethylhexylate, glyceryl tri-2-ethylhexylate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, cetostearyl alcohol, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate and triethyl citrate; silicones such as chain polysiloxanes including dimethylpolysiloxane, methylphenylpolysiloxane, and methylhydrogenpolysiloxane, ring polysiloxanes including decamethylpolysiloxane, dodecamethylpolysiloxane, and tetramethyltetrahydrogenpolysiloxane, as well as silicone resin and silicone rubber which form three-dimensional networks; anionic surfactants such as fatty acid soaps including soap base, sodium laurate and sodium palmitate, higher alkylsulfuric ester salts including sodium laurylsulfate and potassium lauryl sulfate, alkyl ether sulfuric ester salts including triethanolamine POE laurylsulfate and sodium POE laurylsulfate, N-acylsarcosinic acids including sodium lauroylsarcosinate, higher fatty acid amide sulfonates including sodium N-myristoyl-N-methyltaurate, sodium methyltaurid cocoate and sodium laurylmethyltaurid, phosphoric ester salts including sodium POE oleyl ether phosphate and POE stearyl ether phosphoric acid, sulfosuccinates including sodium di-2-ethylhexylsulfosuccinate, sodium monolauroylmonoethanolamide polyoxyethylenesulfosuccinate and sodium laurylpolypropylene glycol sulfosuccinate, alkylbenzenesulfonates including sodium linear dodecylbenzenesulfonate, triethanolamine linear dodecylbenzenesulfonate and linear dodecylbenzenesulfonic acid, N-acylglutamates including monosodium N-lauroylglutamate, disodium N-stearoylglutamate and monosodium N-myristoyl-L-glutamate, higher fatty acid sulfates including sodium hydrogenated glyceryl cocoate sulfate, sulfated oils including turkey red oil, as well as POE alkyl ether carboxylate, POE alkylaryl ether carboxylate, α-olefinsulfonates, higher fatty acid ester sulfonate, sec-alcohol sulfate, higher fatty acid alkyloyl amide sulfate, sodium lauroyl monoethanolamine succinate, ditriethanolamine N-palmitoylaspartate and sodium caseinate; cationic surfactants such as alkyltrimethyl ammonium salts including stearyltrimethyl ammonium chloride and lauryltrimethyl ammonium chloride, distearyl dimethyl ammonium chloride; dialkyl dimethyl ammonium chloride, alkylpyridinium salts including poly (N,N'-dimethyl-3,5-methylene pyridinium) chloride and cetyl pyridinium chloride, as well as alkyl quarternary ammonium salt, alkyldimethylbenzyl ammonium salt, alkylisoquinolinium salt, dialkylmorpholine salt, POE alkylamine, alkylamine salt, polyamine fatty acid derivatives, amylalcohol fatty acid derivatives, benzalkonium chloride and benzetonium chloride; ampholytic surfactants such as imidazoline type ampholytic surfactants including 2-undecyl-N,N,N-(hydroxyethylcarboxymethyl)-2-imidazoline sodium salt and 2-cocoyl-2-imidazaliniumhydroxide-1-carboxyethyloxy 2 sodium salt and betaine type surfactants including 2-heptadecyl-N-carboxymethyl-N-hydroxyethyl imidazolinium betaine, betaine lauryldimethylamino acetate, alkyl betaine, amide betaine and sulfobetaine; lipophilic non-ionic surfactants such as sorbitan fatty acid esters including sorbitan moonlight, sorbitan monoisostearate, sorbitan monolaurate, sorbitan monopalmitate, sorbitan monostearate, sorbitan sesquioleate, sorbitan trioleate, diglycerolsorbitan penta-2-ethylhexylate and diglycerolsorbitan tetra-2-ethylhexylate, glycerol polyglycerol fatty acids including monocottonseed-fatty acid glyceryl ester, glyceryl monoerucate, glyceryl monostearate, glyceryl $\alpha$, $\alpha'$-oleate pyroglutamate and glyceryl monostearate monomalate, propylene glycol fatty acid esters including propylene glycol monostearate, as well as hardened castor oil derivatives, glycerol alkyl ether and polyoxyethylene/methylpolysiloxane copolymer; hydrophilic non-ionic surfactants such as POE sorbitan fatty acid esters including POE-sorbitan monooleate, POE-sorbitan monostearate, POE-sorbitan monooleate and POE-sorbitan tetraoleate, POE-sorbitol fatty acid esters including POE-sorbitol monolaurate, POE-sorbitol monooleate, POE-sorbitol pentaoleate and POE-sorbitol monostearate, POE-glycerol fatty acid esters including POE-glyceryl monostearate, POE-glyceryl monoisostearate and POE-glyceryl triisostearate, POE fatty acid esters including POE monooleate, POE distearate, POE monodioleate and ethylene glycol distearate; POE alkyl ethers including POE lauryl ether, POE oleyl ether, POE stearyl ether, POE behenyl ether, POE2-octyldodecyl ether and POE cholestanol ether, POE alkylphenyl ethers including POE octylphenyl ether, POE nonylphenylether and POE dinonylphenyl ether; pluaronics including pluronic, POE-POP alkyl ethers including POE-POP cetyl ether, POE-POP2-decyltetradecyl ether, POE-POP monobutyl ether, POE-POP hydrogenated lanolin and POE-POP glycerol ether, tetra POE-tetra POP ethylenediamine condensates including tetronic, POE castor oil hardened castor oil derivatives including POE castor oil, POE hardened castor oil, POE hardened castor oil monoisostearate, POE hardened castor oil triisostearate, POE hardened castor oil monopyroglutamate monoisostearate, POE hardened castor oil maleate, POE honeybee wax/lanolin derivatives including POE sorbitol honey bee, alkanol amides including coconut fatty acid diethanol amide, lauric acid monoethanol amide and fatty acid isopropanol amide; as well as POE propylene glycol fatty acid ester, POE alkyl amine, POE fatty acid amide, sucrose fatty acid ester, POE nonylphenylformaldehyde condensate, alkylethoxydimethylamine oxide and trioleyl phosphate; preservatives including methyl paraben, ethyl paraben, and butyl paraben; sequestering agents including sodium edetate and EDTA; natural water soluble polymers such as plant polymers including arabic gum, tragacanth gum, galactan, guar gum, carob gum, karaya gum, carrageenan, pectin, agar, quince seed (Cydonia oblonga), algae colloid (brown algae extract), starch (rice, corn, potatos, or wheat), and glycyrrhizic acid, microbial polymers including xanthangum, dextran, succinoglucane and pullulan, and animal polymers including collagen, casein, albumin and gelatin; semi-synthesized water soluble polymers such as starch type polymers including carboxymethyl starch and methylhydroxypropyl starch, cellulose type polymers including nitrocellulose, ethyl cellulose, methylhydroxypropyl cellulose, hydroxyethyl cellulose, sodium cellulose sulfate, hydroxypropyl cellulose, sodium carboxymethyl cellulose (CMC) crystalline cellulose and cellulose powder, alginic acid type polymers including sodium alginate and propyleneglycol alginate ester; synthesized water soluble polymers such as vinyl type polymers including polyvinyl alcohol, polyvinylmethyl ether, polyvinyl pyrolidone and carboxyvinyl polymer, polyoxyethylene type polymers including polyethylene glycols 2,000, 4,000 and 6,000, polyoxyethylene polyoxypropylene copolymer copolymerization type polymer, acrylic polymers including sodium polyacrylate, polyethyl acrylate and polyacryl amide, as well as polyethylene imine and cation polymer; inorganic water soluble polymers such as bentonite, AlMg silicate (beegum), laponite, hectorite and anhydrous silicic acid; thickeners include casein, dextrin, gelatin, sodium pectate, methyl cellulose, CMC, hydroxyethyl cellulose, hydroxypropyl cellulose, PVA, PVM, PVP, sodium polyacrylate, carboxyvinyl polymer, locust bean gum, guar gum, tamarind gum, cellulose dialkylmethyl ammonium sulfate, xanthangum, aluminum magnesium silicate, bentonite and hectorite; powder ingredients such as inorganic powders including sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstate, magnesium, silica, zeolite, barium sulfate, burned calcium sulfate (calcined gypsum), calcium phosphate, fluorine-apatite, hydroxyapatite, ceramic powder, metal soap (zinc myristate, calcium palmitate, aluminum stearate) and boron nitride, organic powders including polyamide resin powder (nylon powder), polyethylene powder, polymethyl methacrylate powder, polystyrene powder, styrene/acrylic acid copolymer resin powder, benzoguanamine resin powder, polyethylene tetrafluoride powder and cellulose powder; coloring agents such as inorganic white pigments including titanium dioxide and zinc oxide, inorganic red pigments including iron oxide (red iron oxide) and iron titanate, inorganic brown pigments including $\lambda$-iron oxide, inorganic yellow pigments including yellow iron oxide and loess, inorganic black pigments including black iron oxide, carbon black and low oxides of titanium, inorganic purple pigments including mango violet and cobalt violet, inorganic green pigments including chrome oxide, chrome hydroxide and cobalt titanate, inorganic blue pigments including ultramarine blue and Berlin blue; pearl pigments including titanium oxide-coated mica, titanium oxide-coated bismuth oxychloride, titanium oxide-coated talc, colored titanium oxide-coated mica, bismuth oxychloride and fish scale flakes, metal powder pigments including aluminum powder and copper powder, organic pigments including red 201, red 202, red 204, red 205, red 220, red 226, red 228, red 405, orange 203, orange 204, yellow 205, yellow 401 and blue 404, zirconium, barium or aluminum lake organic pigments including red 3, red 104, red 106, red 227, red 230, red 401, red 505, orange 205, yellow 4, yellow 5, yellow 202, yellow 203, green 3 and blue 1, natural colors including chlorophyll and β-carotene, as well as titanium yellow, carthamin, and safflower red; and perfumes, water, alcohol, etc. Specific recipes of the endermic liniment of the present invention are described in the Examples below.

EXAMPLES

The present invention is described in detail below by referring to examples. The technical scope of the present invention is not limited to these examples. The blend ratio is indicated in wt % unit unless specified otherwise.

"Thiol compound stabilization test"

Stabilization of the odor of glutathione was tested by evaluating the odor after adding powders of salts and oxides or various metals. Powder mixed aqueous solutions with the following recipes were let stand for two months at 50° C., and a panel of three specialists conducted a sensory evaluation of the changes in the odor using the following criteria. The results are shown in Table 1.

"Evaluation criteria"

◎: No unpleasant odor was detected.
○: Almost no unpleasant odor was detected.
Δ: A small amount of unpleasant odor was detected.
×: unpleasant odor was detected.

TABLE 1

"Recipe for the powder mixed aqueous solution"

| Ion-exchanged water | 98.0 wt % |
|---|---|
| Glutathione | 1.0 |
| Metal powder (as listed in Table 1) | 1.0 |

| Metal powder | Evaluation result |
|---|---|
| Control (99% ion-exchanged water and 1% glutathione) | x |
| Aluminum oxide | x |
| Aluminum sulfate | x |
| Magnesium chloride | x |
| Magnesium sulfate | x |
| Magnesium nitrate | x |
| Ferrous sulfate | x |
| Titanium oxide | x |
| Titanium oxide treated with alumina | x |
| Zinc sulfate | x |
| Zinc carbonate | x |
| Zinc flower (average particle size: 1 micrometer) | o |
| Ultrafine particle zinc oxide (average particle size: 0.1 micrometers) | ◎ |
| Fine particle zinc oxide treated with dextrin palmitate (average particle size: 0.1 micrometers) | ◎ |

As shown in Table 1, the powder mixed aqueous solution with glutathione and added zinc oxide did not have a unpleasant odor and was stable. A particularly superior effect was exhibited when using fine particle zinc oxide with an average particle size of 0.1 micrometers. Therefore, a stable endermic liniment with no unpleasant odor can be manufactured by adding zinc oxide to glutathione.

Emulsions were prepared using the recipes listed in the following Table 2, Table 3, and Table 4, and the same efficacy test as described above was carried out. The results are shown in the Tables.

TABLE 2

| | Example | | | | | | Comparative example |
|---|---|---|---|---|---|---|---|
| | 1 | 2 | 3 | 4 | 5 | 6 | 1 |
| Liquid paraffin | 30.0 | 30.0 | 30.0 | 30.0 | 30.0 | 30.0 | 30.0 |
| 2-hydroxy-4-methoxybenzophenone | 5.0 | — | 5.0 | 5.0 | 5.0 | 5.0 | 5.0 |
| Cetyl 2-ethyl-hexanoate | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 |
| Decamethyl-cyclopentasiloxane | 20.0 | 20.0 | 20.0 | 20.0 | 20.0 | 20.0 | 20.0 |
| Polyoxyalkylene modified organopolysiloxane | 1.0 | 1.0 | 1.0 | 1.0 | 1.0 | 1.0 | 1.0 |
| Fine particle zinc oxide (average particle size: 0.02 micrometers) | 5.0 | 5.0 | 5.0 | 5.0 | 5.0 | 5.0 | — |
| Organic modified bentonite | 1.5 | 1.5 | 1.5 | 1.5 | 1.5 | 1.5 | 1.5 |
| 1,3-butylene glycol | 5.0 | 5.0 | — | 5.0 | 5.0 | 5.0 | 5.0 |
| EDTA. 3Na. 2H$_2$O | 0.5 | 0.5 | 0.5 | — | 0.5 | 0.5 | 0.5 |
| Tocopherol acetate | 1.0 | 1.0 | 1.0 | 1.0 | — | 1.0 | 1.0 |
| Methyl paraben | 0.5 | 0.5 | 0.5 | 0.5 | 0.5 | — | 0.5 |
| Glutathione | 1.0 | 1.0 | 1.0 | 1.0 | 1.0 | 1.0 | 1.0 |
| Purified water | Balance | Balance | Balance | Balance | Balance | Balance | Balance |
| Evaluation of odor | ◎ | ◎ | ◎ | ◎ | ◎ | ◎ | X |

TABLE 3

| | Example | | | | | | Comparative example |
|---|---|---|---|---|---|---|---|
| | 7 | 8 | 9 | 10 | 11 | 12 | 2 |
| Liquid paraffin | 30.0 | 30.0 | 30.0 | 30.0 | 30.0 | 30.0 | 30.0 |
| 2-hydroxy-4-methoxybenzophenone | 5.0 | — | 5.0 | 5.0 | 5.0 | 5.0 | 5.0 |
| Cetyl 2-ethyl-hexanoate | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 |
| Decamethyl-cyclopentasiloxane | 20.0 | 20.0 | 20.0 | 20.0 | 20.0 | 20.0 | 20.0 |
| Polyoxyalkylene modified organopolysiloxane | 1.0 | 1.0 | 1.0 | 1.0 | 1.0 | 1.0 | 1.0 |
| Fine particle zinc oxide (average particle size: 0.04 micrometers) | 5.0 | 5.0 | 5.0 | 5.0 | 5.0 | 5.0 | — |
| Organic | 1.5 | 1.5 | 1.5 | 1.5 | 1.5 | 1.5 | 1.5 |

TABLE 3-continued

|  | Example | | | | | | Comparative example |
|---|---|---|---|---|---|---|---|
|  | 7 | 8 | 9 | 10 | 11 | 12 | 2 |
| modified bentonite | | | | | | | |
| 1,3-butylene glycol | 5.0 | 5.0 | — | 5.0 | 5.0 | 5.0 | 5.0 |
| EDTA. 3Na. 2H$_2$O | 0.5 | 0.5 | 0.5 | — | 0.5 | 0.5 | 0.5 |
| Tocopherol acetate | 1.0 | 1.0 | 1.0 | 1.0 | — | 1.0 | 1.0 |
| Methyl paraben | 0.5 | 0.5 | 0.5 | 0.5 | 0.5 | — | 0.5 |
| N-acetyl cysteine | 1.0 | 1.0 | 1.0 | 1.0 | 1.0 | 1.0 | 1.0 |
| Purified water | Balance | Balance | Balance | Balance | Balance | Balance | Balance |
| Evaluation of odor | ◉ | ◉ | ◉ | ◉ | ◉ | ◉ | X |

TABLE 4

|  | Example | | | | | | Comparative example |
|---|---|---|---|---|---|---|---|
|  | 13 | 14 | 15 | 16 | 17 | 18 | 3 |
| Liquid paraffin | 30.0 | 30.0 | 30.0 | 30.0 | 30.0 | 30.0 | 30.0 |
| 2-hydroxy-4-meth oxybenzophenone | 5.0 | — | 5.0 | 5.0 | 5.0 | 5.0 | 5.0 |
| Cetyl 2-ethylhexanoate | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 |
| Decamethyl-cyclopenta-siloxane | 20.0 | 20.0 | 20.0 | 20.0 | 20.0 | 20.0 | 20.0 |
| Polyoxy-alkylene modified organopoly-siloxane | 1.0 | 1.0 | 1.0 | 1.0 | 1.0 | 1.0 | 1.0 |
| Fine particle zinc oxide (average particle size: 0.04 micrometers) | 5.0 | 5.0 | 5.0 | 5.0 | 5.0 | 5.0 | 5.0 |
| Organic modified bentonite | 1.5 | 1.5 | 1.5 | 1.5 | 1.5 | 1.5 | 1.5 |
| 1,3-butylene glycol | 5.0 | 5.0 | — | 5.0 | 5.0 | 5.0 | 5.0 |
| EDTA. 3Na. 2H$_2$O | 0.5 | 0.5 | 0.5 | — | 0.5 | 0.5 | 0.5 |
| Tocopherol acetate | 1.0 | 1.0 | 1.0 | 1.0 | — | 1.0 | 1.0 |
| Methyl paraben | 0.5 | 0.5 | 0.5 | 0.5 | 0.5 | — | 0.5 |
| Glutathione | 5.0 | 5.0 | 5.0 | — | — | — | 5.0 |
| N-acetyl cysteine | — | — | — | 5.0 | 5.0 | 5.0 | — |
| Antioxidant ① | — | 1.0 | — | — | 1.0 | — | 1.0 |
| Antioxidant ② | — | — | 1.0 | — | — | 1.0 | — |
| Purified water | Balance | Balance | Balance | Balance | Balance | Balance | Balance |
| Evaluation of odor | ○ | ◉ | ◉ | ○ | ◉ | ◉ | X |

Antioxidant ①: Dibutylhydroxytoluene
Antioxidant ②: Butylhydroxyanisole

As shown in Table 2, Table 3, and Table 4, the endermic liniments of the Examples which contain zinc oxide did not have a unpleasant odor and were very stable. When antioxidants were added, a superior stabilization effect was exhibited even when a high concentration of a thiol compound was contained.

Other examples of the endermic liniment of the present invention are shown below. For every example, the thiol compound in the recipe was stable after two months at 50° C. and no unpleasant odor was observed. The endermic liniment of the present invention was thus proven to be able to exhibit the effect of the present invention in any formulation.

Example 19

Gel with powder

A gel of the following recipe was prepared by stirring and dissolving the water phase, then adding the alcohol phase to it, followed by stirring.

| Ingredients | Blend ratio wt % |
|---|---|
| A. Water phase | |
| Purified water | Balance |
| Polyethylene glycol 400 | 5.0 |
| Propylene glycol | 5.0 |
| Dipotassium glycyrrhizate | 0.1 |
| Sodium hyaluronate | 0.05 |
| Carboxyvinyl polymer | 0.5 |
| Caustic potash | 0.2 |
| Sodium hydroxymethoxybenzophenone sulfonate | 0.1 |
| Glutathione | 0.5 |
| Fine particle zinc oxide (average particle 0.04 micrometers) | 0.5 |
| B. Alcohol phase | |
| Ethanol | 10.0 |
| POE (25) octyldodecyl ether | 0.5 |
| 2-ethylhexyl paramethoxycinnamate | 0.05 |
| Tocopherol acetate | 0.1 |
| Methyl paraben | 0.1 |
| Perfume | Appropriate amount |

Example 20

Emulsion

An emulsion with the following recipe was prepared by adding the oil phase ingredients to the water phase ingredients while emulsifying with an emulsifier.

| Ingredients | Blend ratio wt % |
|---|---|
| A. Oil phase | |
| Stearic acid | 2.0 |
| Cetanol | 1.0 |
| Vaseline | 2.0 |
| Liquid paraffin | 9.0 |
| Cetyl 2-ethylhexanoate | 1.0 |
| Jojoba oil | 1.0 |
| Squalane | 2.0 |
| Pentaerythritol tetra-2-ethylhexanoate | 3.0 |
| Methylphenylpolysiloxane | 2.0 |
| Evening primrose oil | 0.5 |
| Glyceryl diparamethoxycinnamate mono-2-ethylhexanoate | 1.5 |
| POE (10) monooleate | 0.1 |
| Fine particle zinc oxide treated with stearic acid | 5.0 |

-continued

| Ingredients | Blend ratio wt % |
|---|---|
| (average particle size: 0.02 micrometers) | |
| Butyl paraben | 0.2 |
| Perfume | Appropriate amount |
| B. Water phase | |
| Propylene glycol | 5.0 |
| 1,3-butylene glycol | 2.0 |
| Arbutin | 5.0 |
| Carboxyvinyl polymer | 0.2 |
| Triethanolamine | 0.2 |
| N-acetylcysteine | 3.0 |
| Zinc flower | 5.0 |
| Purified water | Balance |

Example 21

Cream

A cream with the following recipe was prepared by adding the oil phase ingredients to the water phase ingredients while emulsifying with an emulsifier.

| Ingredients | Blend ratio wt % |
|---|---|
| A. Oil phase | |
| Stearic acid | 2.0 |
| Stearyl alcohol | 7.0 |
| Reduced lanolin | 2.0 |
| Olive Oil | 1.0 |
| Glyceryl tri-2-ethylhexanoate | 3.0 |
| Octyldodecanol | 5.0 |
| POE (25) cetyl ether | 3.0 |
| Glyceryl monostearate | 2.0 |
| 2-ethylhexyl paradimethylaminobenzoate | 0.5 |
| 2-hydroxy-4-methoxybenzophenone | 0.5 |
| Zinc oxide treated with dextrin palmitate (average particle size: 0.04 micrometers) | 5.0 |
| Propyl paraben | 0.3 |
| Perfume | Appropriate amount |
| B. Water phase | |
| 1,3-butylene glycol | 6.0 |
| Dipropylene glycol | 3.0 |
| Glycerine | 4.0 |
| Tranexamic acid | 2.0 |
| Magnesium phosphate-L-ascorbate | 0.1 |
| Pantothenic acid | 0.1 |
| Glutathione | 2.0 |
| Purified water | Balance |

Example 22

Two-phase type toilet water

A two-phase type toilet water of the following recipe was prepared by stirring and dissolving the water phase, then adding the alcohol phase to it.

| Ingredients | Blend ratio wt % |
|---|---|
| A. Water phase | |
| Purified water | Balance |
| Propylene glycol | 4.0 |
| Allantoin | 0.2 |

-continued

| Ingredients | Blend ratio wt % |
|---|---|
| Common salt | 0.1 |
| Bentonite | 1.0 |
| Talc | 0.5 |
| Cellulose powder | 0.5 |
| Silica | 1.0 |
| Sodium hydroxymethoxybenzophenoneslufonate | 0.1 |
| Glutathione | 0.5 |
| Fine particle zinc oxide (average particle size: 0.02 micrometers) | 1.0 |
| B. Alcohol phase | |
| Ethanol | 15.0 |
| Methyl paraben | 0.1 |
| Menthol | 0.05 |
| POE (60) glyceryl monoisostearate | 0.5 |
| Tocopherol acetate | 0.01 |
| Perfume | Appropriate amount |

Example 23

Peel-off type pack

A peel-off type pack of the following recipe was prepared by stirring and dissolving the water phase, then adding the alcohol phase to it.

| Ingredients | Blend ratio wt % |
|---|---|
| A. Water phase | |
| Purified water | Balance |
| Polyethylene glycol 1500 | 5.0 |
| Polyvinyl alcohol | 13.0 |
| Placenta extract | 0.3 |
| N-acetylcysteine | 0.5 |
| Zinc flower | 1.0 |
| Fine particle zinc oxide (average particle size: 0.1 micrometers) | 1.0 |
| B. Alcohol phase | |
| Ethanol | 7.0 |
| POE (20) oleyl alcohol ether | 1.0 |
| Methyl paraben | 0.2 |
| Fine particle zinc oxide treated with myristic acid | 1.0 |
| Perfume | Appropriate amount |

Example 24

Sunscreen cream

A sunscreen cream of the following recipe was prepared by adding the oil phase ingredients to the water phase ingredients while emulsifying with an emulsifier.

| Ingredients | Blend ratio wt % |
|---|---|
| A. Oil phase | |
| Octylmethoxy cinnamate | 5.0 |
| Decamethylcyclopentasiloxane | 20.0 |
| Methylpolysiloxane | 5.0 |
| POE glycerol triisostearic ester | 1.5 |
| Organic modified clay mineral (Benton 38) | 0.5 |
| Silicone resin | 5.0 |
| Vitamin E acetate | 0.05 |

-continued

| Ingredients | Blend ratio wt % |
|---|---|
| Methyl paraben | 0.5 |
| Titanium oxide treated with alumina | 5.0 |

Zinc oxide treated with silicone (average particle size: 0.02 micrometers; the silicone treatment was carried out by using the method described in Japanese examined patent publication Tokko Hei 1-54381.)

| Perfume | Appropriate amount |
|---|---|
| B. Water phase | |
| 1,3-butylene glycol | 5.0 |
| Glycerine | 5.0 |
| E15TA 3Na-2H$_2$O | 0.5 |
| Glutathione | 1.0 |
| Purified water | Balance |

Industrial Applicability of the Invention

As described thus far, the present invention provides an endermic liniment which prevents a unpleasant odor due to aging of the thiol compound and has significantly improved stability over time.

What is claimed is:

1. An endermic liniment comprising a thiol compound and zinc oxide having an average particle size of from 0.001–0.2 micrometers, said zinc oxide having a water repellant treatment on its surface in which a water repellant treatment is selected from the group consisting of myristic acid treatment, zinc myristate treatment, aluminum myristate treatment, palmitic acid treatment, dextrin palmitic acid treatment, zinc palmitate treatment, aluminum palmitate treatment, dextrin stearic acid treatment, zinc stearate treatment, and aluminum stearate treatment.

2. The endermic liniment of claim 1, wherein said thiol compound is selected from the group consisting of cysteine and its derivatives.

3. The endermic liniment of claim 1, wherein said thiol compound is selected from the group consisting of glutathione and its derivatives.

4. The endermic liniment of claim 2, wherein the content of said thiol compound comprises from 0.001 to 20.0 wt % of said liniment.

5. The endermic liniment of claim 3, wherein said thiol compound comprises from 0.001 to 20.0 wt % of said liniment.

* * * * *